United States Patent
Ito

(10) Patent No.: US 10,049,480 B2
(45) Date of Patent: Aug. 14, 2018

(54) IMAGE ALIGNMENT DEVICE, METHOD, AND PROGRAM

(71) Applicant: FUJIFILM Corporation, Tokyo (JP)

(72) Inventor: Hirotaka Ito, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 12 days.

(21) Appl. No.: 15/228,506

(22) Filed: Aug. 4, 2016

(65) Prior Publication Data

US 2017/0061611 A1    Mar. 2, 2017

(30) Foreign Application Priority Data

Aug. 31, 2015  (JP) .................................. 2015-169986

(51) Int. Cl.
*G06K 9/00* (2006.01)
*G06T 11/60* (2006.01)
(Continued)

(52) U.S. Cl.
CPC ............... *G06T 11/60* (2013.01); *A61B 6/03* (2013.01); *A61B 6/037* (2013.01); *A61B 90/36* (2016.02); *G06T 7/337* (2017.01); *A61B 5/055* (2013.01); *A61B 2034/2048* (2016.02); *A61B 2090/365* (2016.02); *A61B 2090/3612* (2016.02);
(Continued)

(58) Field of Classification Search
CPC .............. A61B 2090/365; A61B 5/055; A61B 2034/105; A61B 2090/364; A61B 34/25; A61B 2034/2065; A61B 2090/3612; A61B 2090/366; A61B 34/10; A61B 34/20;
(Continued)

(56) References Cited

U.S. PATENT DOCUMENTS 5,765,561 A     6/1998  Chen et al.
2004/0215071 A1* 10/2004  Frank .................. A61B 6/4441
                                                     600/407
(Continued)

FOREIGN PATENT DOCUMENTS

JP    2010-200894 A    9/2010
JP    2010-259497 A    11/2010
(Continued)

OTHER PUBLICATIONS

Japanese Office Action dated May 29, 2018 for corresponding Application No. 2015-169986 (with English translation).

*Primary Examiner* — Li Liu
(74) *Attorney, Agent, or Firm* — Birch, Stewart, Kolasch & Birch, LLP

(57) ABSTRACT

There is provided an image registration device, method, and program that enable easy and quick initial registration between a target part included in an intraoperative video and simulation information, such as a simulation image. A first registration unit performs initial registration between an intraoperative video and simulation information. At this time, an intraoperative image for registration in an intraoperative video is displayed on a display. An operator performs registration between a target part included in the intraoperative image and the simulation information. After the end of initial registration, a second registration unit performs second registration between the simulation information and the target part included in the intraoperative video based on the result of the initial registration.

18 Claims, 6 Drawing Sheets

(51) Int. Cl.
*A61B 6/03* (2006.01)
*A61B 90/00* (2016.01)
*G06T 7/33* (2017.01)
*A61B 5/055* (2006.01)
*A61B 34/20* (2016.01)

(52) U.S. Cl.
CPC . *A61B 2505/05* (2013.01); *G06T 2207/10016* (2013.01); *G06T 2207/10072* (2013.01); *G06T 2207/20221* (2013.01)

(58) Field of Classification Search
CPC ....... A61B 5/7425; A61B 6/466; A61B 90/37; G06T 19/006; G06T 2207/20221; G06T 7/38
See application file for complete search history.

(56) References Cited

U.S. PATENT DOCUMENTS

| | | | | |
|---|---|---|---|---|
| 2005/0215879 | A1* | 9/2005 | Chuanggui | G06T 7/001 600/407 |
| 2008/0089566 | A1* | 4/2008 | Node-Langlois | G06T 7/30 382/128 |
| 2008/0119725 | A1* | 5/2008 | Lloyd | A61B 90/36 600/424 |
| 2012/0029387 | A1* | 2/2012 | Wei | A61B 90/36 600/587 |
| 2012/0253170 | A1 | 10/2012 | Kim et al. | |
| 2012/0253200 | A1* | 10/2012 | Stolka | A61B 1/041 600/459 |
| 2013/0176336 | A1 | 7/2013 | Hannula | |
| 2014/0241600 | A1* | 8/2014 | Mountney | G06T 17/00 382/128 |
| 2015/0051617 | A1 | 2/2015 | Takemura et al. | |
| 2016/0063707 | A1* | 3/2016 | Masumoto | G06T 11/20 345/419 |
| 2016/0078633 | A1* | 3/2016 | Tahmasebi Maraghoosh | G06T 17/20 382/131 |
| 2017/0007350 | A1* | 1/2017 | Popovic | A61B 1/00009 |
| 2017/0069073 | A1* | 3/2017 | Sela | A61B 34/10 |
| 2017/0172663 | A1* | 6/2017 | Popovic | A61B 34/10 |

FOREIGN PATENT DOCUMENTS

| | | |
|---|---|---|
| JP | 2011-8397 A | 1/2011 |
| JP | 2012-205899 A | 10/2012 |
| JP | 2013-202313 A | 10/2013 |
| JP | 2014-522274 A | 9/2014 |

* cited by examiner

IMAGE ALIGNMENT DEVICE, METHOD, AND PROGRAM

CROSS-REFERENCE TO RELATED APPLICATIONS

The present application claims priority under 35 U.S.C. § 119 to Japanese Patent Application No. 2015-169986, filed on Aug. 31, 2015, all of which are hereby expressly incorporated by reference into the present application.

BACKGROUND OF THE INVENTION

1. Field of the Invention

The present invention relates to an image registration device, method, and non-transitory computer readable recording medium storing a program for registrating an intraoperative image including a target part of surgery, which is captured during the surgery, and simulation information relevant to the surgery of the target part and displaying the intraoperative image and the simulation information after the registration so as to be superimposed on each other.

2. Description of the Related Art

In recent years, surgical simulation using a three-dimensional medical image has been actively performed. Surgical simulation is for visualizing surgery target tissue, organs, and surrounding structures thereof in a medical image and simulating the procedure performed in actual surgery. For example, in a partial resection simulation of the liver, a simulation image viewed from the operative field at the time of surgery is generated by extracting tissues, such as the liver, the portal vein, veins, arteries, the body surface, bone, and a tumor, from a computed tomography (CT) image or a magnetic resonance imaging (MRI) image and visualizing the tissues as a three-dimensional image. Then, a range for excising a tumor in the liver is calculated by a computer using the simulation image, and a surgical plan is made to perform the surgery.

On the other hand, there is a desire to see the simulation image during surgery. For this reason, paper on which a simulation image is printed is brought to the operating room, or the simulation image is displayed on a display installed in the operating room. Then, a doctor performs the surgery while watching the operative part of the actual patient and while viewing the simulation image printed on paper or displayed on the display for the sake of confirmation.

However, it is very troublesome to perform the surgery while alternately viewing the patient and the simulation image. Therefore, a method of acquiring a video including a plurality of images by imaging a surgery target part during the surgery and superimposing a simulation image on the video has been proposed. For example, JP2013-202313A has proposed a method of attaching an optical sensor or a magnetic sensor directly to a camera for imaging an operative part, a surgical instrument, or an organ, performing a calibration, that is, initial registration of the relative positional relationship therebetween, registrating a surgery target part and a simulation image by moving the simulation image with respect to changes in the position and direction of the camera and the movement of the organ after the initial registration, and displaying the surgery target part and the simulation image after the registration so as to be superimposed on each other.

In addition, a method of placing a marker in a surgery target part, detecting the position of the marker using a sensor, registrating the surgery target part and a simulation image, and displaying the surgery target part and the simulation image after the registration on a head mounted display (refer to JP2010-259497A) and a method of embedding a marker in a surgery target part, detecting the marker using a sensor, registrating the surgery target part and a simulation image, and displaying the surgery target part and the simulation image after the registration on a monitor (refer to JP2010-200894A) have also been proposed.

On the other hand, a method of registrating an image of a patient who has been imaged and a simulation image without using a sensor or the like has also been proposed. For example, JP2012-205899A has proposed a method in which, when generating an organ model from a three-dimensional image and displaying the organ model so as to be superimposed on an ultrasound image in real time, an affine transformation function between each frame of the ultrasonic image and the organ model is calculated, the organ model is converted based on the affine transformation function, and the converted organ model is superimposed on the ultrasonic image. JP2014-522274A has proposed a method of overlapping induced brain stimulation function data on a live image of the brain during surgery of the brain. In addition, although a medical image is not a target, a method of displaying the template of eyebrows or the like so as to be superimposed on the face image of a user while imaging the face of the user in real time, detecting a change in the angle of the face of the user and the enlargement and reduction of the face of the user, and moving, enlarging, and reducing the template according to the detected changes and enlargement and reduction has also been proposed (refer to JP2011-008397A).

SUMMARY OF THE INVENTION

However, when imaging a target part, as long as the camera is held by the hand, it is difficult to hold the camera completely still. Accordingly, the target part moves in a displayed video. For this reason, it is very difficult for the operator to manually perform initial registration between the target part included in the video and the simulation information. Even in the case of performing the registration automatically as disclosed in JP2012-205899A and JP2014-522274A, if the target part included in the video moves, a long time for the initial registration is required.

The invention has been made in view of the aforementioned situation, and it is an object of the invention to enable easy and quick initial registration between a target part included in an intraoperative video and simulation information, such as a simulation image.

An image registration device according to the invention comprises: image acquisition unit that acquires an intraoperative video that includes a target part of surgery and is configured to include a plurality of intraoperative images captured at different imaging times; simulation information acquisition unit that acquires simulation information relevant to the surgery of the target part; intraoperative image for registration acquisition unit that acquires an intraoperative image for registration used in registration with the simulation information; first registration unit that displays the intraoperative image for registration and the simulation information on display unit such that the intraoperative image for registration and the simulation information are superimposed on each other and performing first registration between the simulation information and the target part included in the intraoperative image for registration; and second registration unit that performs second registration between the simulation information and the target part included in the intraoperative video based on a result of the first registration after an end of the first registration and displaying the simulation information and the target part included in the intraoperative video after the second registration on the display unit such that the simulation information and the target part included in the intraoperative video after the second registration are superimposed on each other.

The "intraoperative video" is a motion picture configured to include a plurality of intraoperative images that are acquired by imaging a target part sequentially at a predetermined frame rate.

The "simulation information" means arbitrary information relevant to a target part of surgery. For example, image information, such as an image showing the three-dimensional shape of a target part, an image showing the three-dimensional shape of a target part and structures included in the target part, or a functional three-dimensional image acquired by positron emission tomography (PET) examination or nuclear medical (NM) examination, can be used as the simulation information. In addition, text information such as the name of a target part and the name of a structure included in the target part, a line indicating the resection position of a target part, and symbols such as arrows can be used as the simulation information.

The image registration device according to the invention may further comprise input unit that receives an input of an instruction of the first registration, and the first registration unit may perform the first registration in response to the instruction of the first registration that is input through the input unit.

The "instruction of the first registration" is an instruction to perform registration between the simulation information and the target part included in the intraoperative image for registration. For example, the "instruction of the first registration" is an instruction to match the simulation information with the target part included in the intraoperative image for registration by parallel movement, rotation, enlargement and reduction, and the like.

In the image registration device according to the invention, the second registration unit may perform the second registration after receiving an instruction to end the first registration.

In the image registration device according to the invention, the second registration unit may perform third registration between the intraoperative image for registration and an intraoperative image, which forms the intraoperative video acquired after the end of the first registration, after the end of the first registration and perform the second registration using a result of the third registration.

The "intraoperative image that forms an intraoperative image" to be aligned with the intraoperative image for registration is preferably an intraoperative image that is acquired first after the end of the first registration. However, the "intraoperative image that forms an intraoperative image" is not limited thereto, and may be an intraoperative image that is acquired with a delay from the end of the first registration to the extent that there is no problem in the observation of the operator in a state in which the simulation information and the target part included in the intraoperative video are displayed so as to be superimposed on each other.

In the image registration device according to the invention, the second registration unit may perform fourth registration between intraoperative images, which form the intraoperative video acquired by the image acquisition unit, until the first registration ends from a start of the first registration, and perform the second registration using a result of the fourth registration after the end of the first registration.

The fourth registration is an registration between intraoperative images acquired in a sequential manner that form an intraoperative video, specifically, between an intraoperative image acquired previously and an intraoperative image acquired later.

The image registration device according to the invention may further comprise motion detection unit that detects movement of imaging unit for imaging the target part to generate the intraoperative image, and the second registration unit may perform the third registration using the movement detected by the motion detection unit until the first registration ends from a start of the first registration.

The image registration device according to the invention may further comprise motion detection unit that detects movement of imaging unit for imaging the target part to generate the intraoperative image, and the second registration unit may perform the fourth registration using the movement detected by the motion detection unit until the first registration ends from a start of the first registration.

The image registration device according to the invention may further comprise motion detection unit that detects movement of imaging unit for imaging the target part to generate the intraoperative image.

In this case, the second registration unit may perform the second registration using the movement detected by the motion detection unit.

In the image registration device according to the invention, the second registration unit may perform the second registration by registrating the simulation information and the target part included in each intraoperative image that forms the intraoperative image.

The image registration device according to the invention may further comprise determination unit that determines whether or not it is possible to perform the second registration and warning unit that gives a warning in a case where it is determined that it is not possible to perform the second registration.

Here, as the surgery progresses, a target part of surgery is excised, or the target part is partially moved. As a result, the appearance of the target part included in the intraoperative image for registration used at the time of the first registration becomes different from the target part included in the intraoperative video acquired at the present time. For this reason, as the surgery progresses, the second registration may be difficult. "It is not possible to perform the second registration" unit a state in which it is not possible to perform registration between the simulation information and the target part included in the intraoperative video with the desired accuracy as the surgery progresses as described above.

An image registration method according to the invention includes: acquiring an intraoperative video that includes a target part of surgery and is configured to include a plurality of intraoperative images captured at different imaging times; acquiring simulation information relevant to the surgery of the target part; acquiring an intraoperative image for registration used in registration with the simulation information; displaying the intraoperative image for registration and the simulation information on display unit such that the intraoperative image for registration and the simulation information are superimposed on each other and performing first registration between the simulation information and the target part included in the intraoperative image for registration; and performing second registration between the simulation information and the target part included in the intraoperative video based on a result of the first registration after an end of the first registration and displaying the simulation information and the target part included in the intraoperative video after the second registration on the display unit such that the simulation information and the target part included in the intraoperative video after the second registration are superimposed on each other.

In addition, a non-transitory computer readable recording medium storing a program causing a computer to execute the image registration method according to the invention may be provided.

According to the invention, the intraoperative image for registration and the simulation information are displayed on the display unit so as to be superimposed on each other, and the first registration between the simulation information and the target part included in the intraoperative image for registration is performed. After the end of the first registration, the second registration between the simulation information and the target part included in the intraoperative video is performed based on the result of the first registration. Thus, at the time of the first registration, since the intraoperative image for registration is displayed, it is possible to easily perform the registration between the intraoperative image and the simulation information. In addition, at the time of the first registration, the intraoperative image for registration is aligned with the simulation information. Therefore, it is possible to quickly perform the first registration processing.

In addition, by performing the first registration in response to an instruction of the first registration that is input through the input unit, it is possible to easily perform the registration between a target part included in the intraoperative image and the simulation information.

DESCRIPTION OF THE PREFERRED EMBODIMENTS

Figure 1:
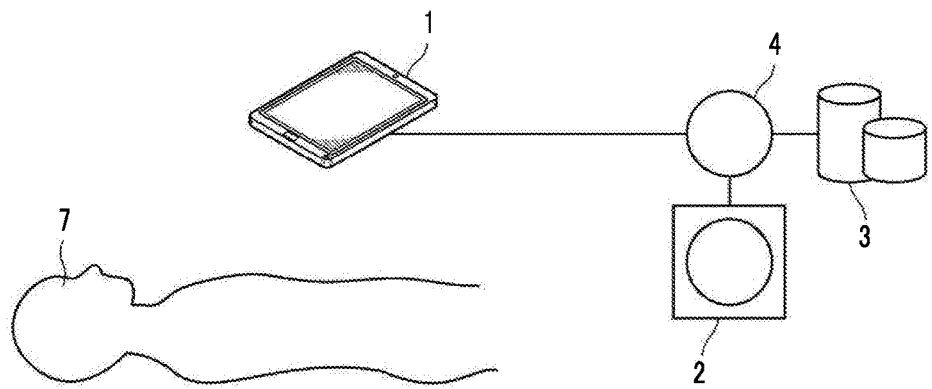
FIG. 1 is a diagram showing the schematic hardware configuration of a surgery assistance system to which an image registration device according to an embodiment of the invention is applied.

Hereinafter, embodiments of the invention will be described with reference to the diagrams. FIG. 1 is a diagram showing the schematic hardware configuration of a surgery assistance system to which an image registration device according to a first embodiment of the invention is applied. As shown in FIG. 1, in this system, an image registration device 1 according to the present embodiment, a three-dimensional imaging apparatus 2, and an image storage server 3 are communicably connected to each other through a network 4.

The three-dimensional imaging apparatus 2 is an apparatus that generates a three-dimensional image V0 showing a part, which is a surgery target in a subject 7, by imaging the part. Specifically, the three-dimensional imaging apparatus 2 is a CT apparatus, an MRI apparatus, a PET apparatus, or the like. The three-dimensional image V0 generated by the three-dimensional imaging apparatus 2 is transmitted and stored in the image storage server 3. In the present embodiment, it is assumed that the surgery target part of the subject 7 is liver, the three-dimensional imaging apparatus 2 is a CT apparatus, and the three-dimensional image V0 of the abdomen of the subject 7 is generated.

The image storage server 3 is a computer that stores and manages various kinds of data, and includes a large-capacity external storage device and software for database management. The image storage server 3 performs communication with other devices through the wired or wireless network 4 to transmit and receive image data or the like. Specifically, the image storage server 3 acquires image data, such as the three-dimensional image V0 generated by the three-dimensional imaging apparatus 2, through the network, and stores the image data in a recording medium, such as a large-capacity external storage device, and manages the image data. The storage format of image data or the communication between devices through the network 4 is based on a protocol, such as a digital imaging and communication in medicine (DICOM).

The image registration device 1 is realized by installing an image registration program of the invention in one computer. In the present embodiment, a computer is a tablet terminal that is directly operated by a doctor, who is an operator of the apparatus, and that is wirelessly connected to the network 4. The registration program is distributed in a state in which the registration program is recorded in a recording medium, such as a digital versatile disc (DVD) or a compact disk read only memory (CD-ROM), and is installed into the tablet terminal from the recording medium. Alternatively, the registration program is stored in a storage device of a server computer connected to the network or in a network storage device so as to be accessible from the outside, and is downloaded and installed into a tablet terminal when necessary.

Figure 2:
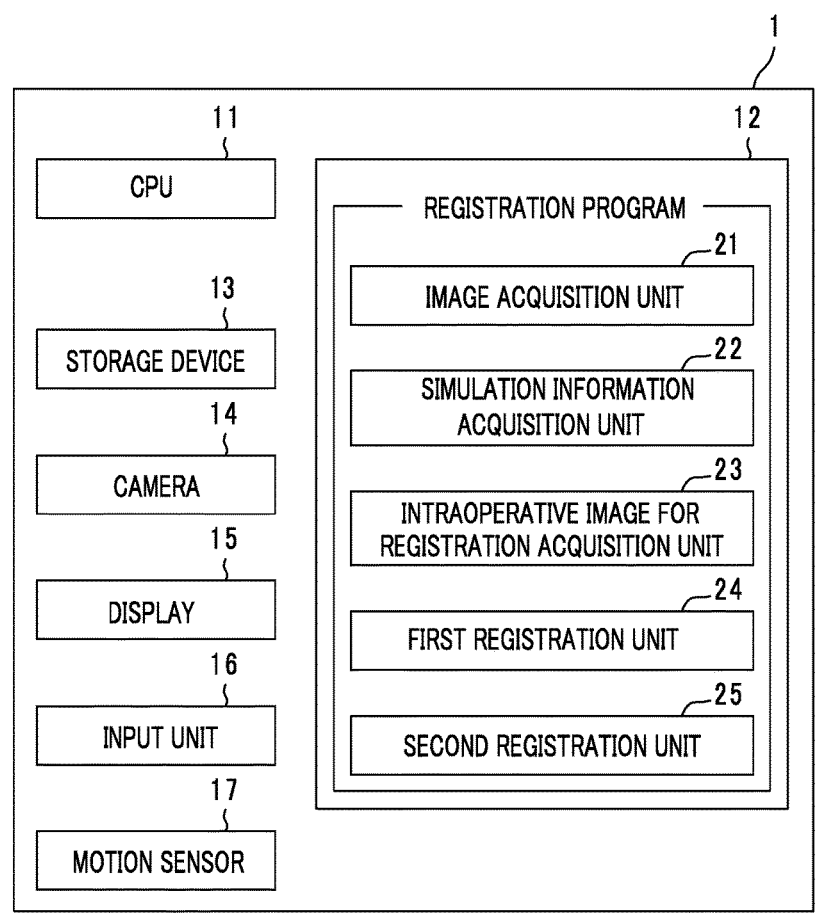
FIG. 2 is a diagram showing the schematic configuration of an image registration device realized by installing an registration program in a tablet terminal.

FIG. 2 is a diagram showing the schematic configuration of an image registration device realized by installing an registration program in a tablet terminal. As shown in FIG. 2, as the configuration of a standard tablet terminal, the image registration device 1 includes a central processing unit (CPU) 11, a memory 12, a storage device 13, a camera 14, a display 15 such as a liquid crystal display, a touch panel type input unit 16, and a motion sensor 17.

Various kinds of information including the three-dimensional image V0, which has been acquired from the image storage server 3 through the network 4, and the image generated by the processing in the image registration device 1 are stored in the storage device 13.

The camera 14 includes a lens, an imaging device such as a charge coupled device (CCD), an image processing unit that performs processing for improving the image quality on the acquired image, and the like. The doctor acquires an intraoperative video L0 including the liver, which is configured to include two or more images captured at different imaging times, by imaging the liver of the subject 7 after laparotomy, which is a surgery target part in the subject 7 during the surgery, using the image registration device 1, that is, the camera 14 of the tablet terminal. The intraoperative video L0 is a motion picture in which intraoperative images T0 are continuous at a predetermined frame rate. The camera 14 corresponds to imaging unit.

The motion sensor 17 is a 9-axis motion sensor that detects the acceleration of three axes of an x axis, a y axis, and a z axis relative to the position of the tablet terminal as a reference, angular velocity of three axes, and the inclination of three axes. Accordingly, the motion sensor 17 detects the movement of the tablet terminal, that is, the movement of the camera 14. The acceleration, the angular velocity, and the inclination detected by the motion sensor 17 are output to the CPU 11 as motion information, and are used in required processing.

In addition, an image registration program is stored in the memory 12. As processing executed by the CPU 11, the image registration program defines image acquisition processing for acquiring the intraoperative video L0 and the three-dimensional image V0, simulation information acquisition processing for acquiring simulation information S0 of the liver that is a target object included in the intraoperative video L0, an intraoperative image for registration acquisition processing for acquiring an initial intraoperative image, which is used for registration with the simulation information S0, as an intraoperative image for registration, first registration processing for performing first registration as initial registration between the liver, which is a target object included in the intraoperative video L0, and the simulation information S0, and second registration processing for performing second registration between the liver included in the intraoperative video L0 and the simulation information S0.

The CPU 11 executes these processes according to the program, so that the tablet terminal functions as an image acquisition unit 21, a simulation information acquisition unit 22, a intraoperative image for registration acquisition unit 23, a first registration unit 24, and a second registration unit 25. In addition, the image registration device 1 may include a processor that performs image acquisition processing, simulation information acquisition processing, first registration processing, and second registration processing.

The image acquisition unit 21 acquires the intraoperative video L0 including a target part of the subject 7 during the surgery captured by the camera 14 and the three-dimensional image V0. In a case where the three-dimensional image V0 is already stored in the storage device 13, the image acquisition unit 21 may acquire the three-dimensional image V0 from the storage device 13. In the present embodiment, the intraoperative video L0 is acquired when a doctor images the liver from above the subject 7 after laparotomy.

The simulation information acquisition unit 22 generates simulation information of the liver that is a surgery target part. Accordingly, the simulation information acquisition unit 22 first extracts the liver that is a surgery target part and hepatic arteries, hepatic veins, and lesions, which are included in the liver, from the three-dimensional image V0. The simulation information acquisition unit 22 includes an identifier for identifying whether or not each pixel in the three-dimensional image V0 is a pixel showing the liver and hepatic arteries, hepatic veins, and lesions included in the liver (hereinafter, referred to as the liver and the like). The identifier acquires a plurality of sample images including the liver and the like by machine learning using a method, such as Ada boosting algorithm. The simulation information acquisition unit 22 extracts the liver and the like from the three-dimensional image V0 using an identifier.

Then, the simulation information acquisition unit 22 generates an image showing the three-dimensional shape of the liver and the like as the simulation information S0. Specifically, a projected image obtained by projecting the extracted liver and the like on a predetermined projection plane is generated as the simulation information S0. Here, the projection plane may be any plane facing the liver of the subject 7 from the front, for example. In addition, as a specific projection method, for example, a known volume rendering method is used.

Figure 3:
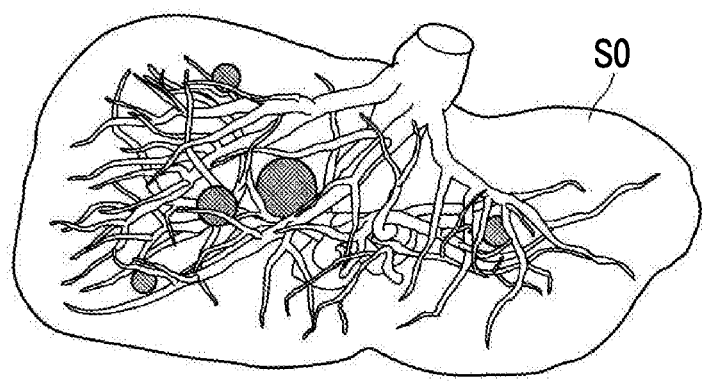
FIG. 3 is a diagram showing the simulation information.

At this time, the simulation information S0 may be generated by defining different colors for the liver and hepatic arteries, hepatic veins, and lesions included in the liver, or the simulation information S0 may be generated by defining different transparencies. For example, red, blue, and green may be set for hepatic arteries, hepatic veins, and lesions, respectively. In addition, the opacity of the liver may be set to 0.1, the opacity of hepatic arteries and hepatic veins may be set to 0.5, and the opacity of lesions may be set to 0.8. In this manner, the simulation information S0 shown in FIG. 3 is generated. Thus, in the simulation information S0, by defining different colors or different opacities for the liver and hepatic arteries, hepatic veins, and lesions included in the liver, it is possible to easily identify the liver and hepatic arteries, hepatic veins, and lesions included in the liver. Alternatively, the simulation information S0 may be generated by defining both different colors and different transparencies. The generated simulation information S0 is stored in the storage device 13.

Hereinafter, the process performed in the present embodiment will be described together with the explanation of the intraoperative image for registration acquisition unit 23, the first registration unit 24, and the second registration unit 25.

Figure 4:
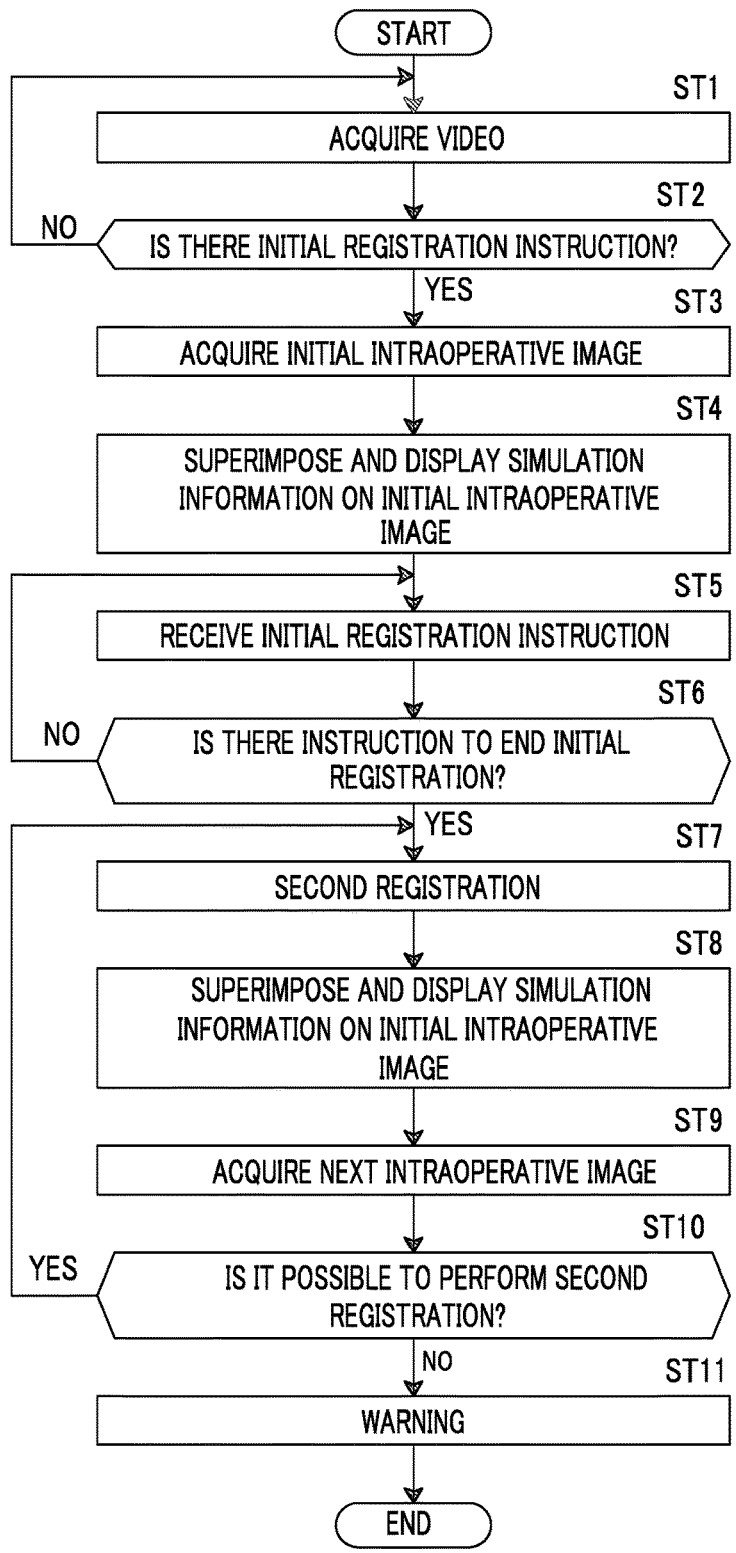
FIG. 4 is a flowchart showing the process performed in a first embodiment.

FIG. 4 is a flowchart showing the process performed in the first embodiment. In addition, it is assumed that the simulation information S0 has already been generated and stored in the storage device 13. First, the intraoperative video L0 is acquired by imaging the liver that is a surgery target part of the subject 7 (step ST1). The intraoperative video L0 is configured to include the intraoperative images T0 that are sequentially acquired at a predetermined frame rate, such as 30 fps. Then, the intraoperative image for registration acquisition unit 23 starts monitoring whether or not there has been an initial registration instruction (step ST2). If the result in step ST2 is positive, the intraoperative image T0 that forms the intraoperative video L0 at a time when there has been an initial registration instruction is acquired as an intraoperative image for initial registration (hereinafter, referred to as an initial intraoperative image) Tf (step ST3). The intraoperative image for registration acquisition unit 23 displays the initial intraoperative image Tf on the display 15, and further displays the simulation information S0 on the display 15. Accordingly, the initial intraoperative image Tf, which is a still image, and the simulation information S0 are displayed on the display 15 so as to be superimposed on each other (step ST4). In this step, the simulation information S0 is displayed at a predetermined position on the display 15. The initial intraoperative image Tf corresponds to an intraoperative image for registration. Then, the first registration unit 24 receives an initial registration instruction from a doctor (step ST5). Then, the first registration unit 24 performs initial registration. In addition, the first registration unit 24 may perform the processing of step ST4.

Figure 5:
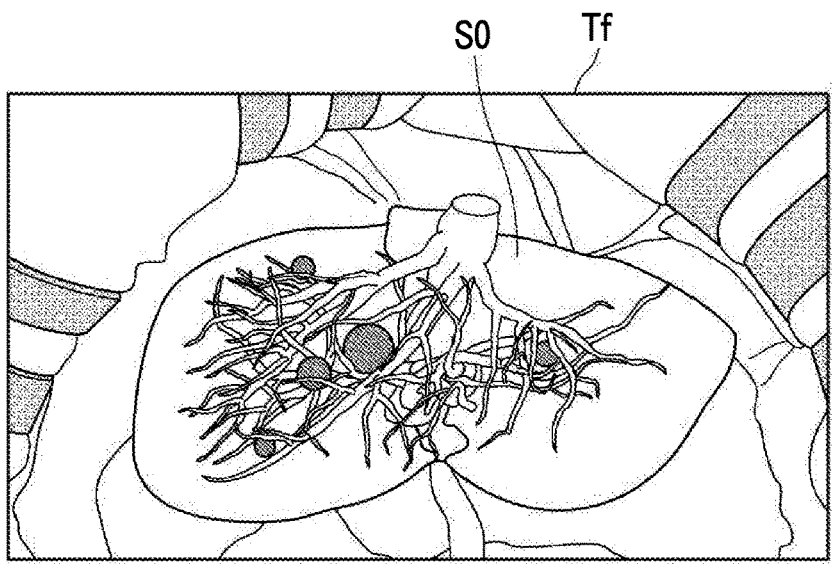
FIG. 5 is a diagram showing an intraoperative image displayed on a display during initial registration.

FIG. 5 is a diagram showing an intraoperative image displayed on a display during initial registration. Parallel movement, rotation, and enlargement and reduction of the simulation information S0 displayed as described above can be realized by operating the input unit 16, that is, by a touch operation on the display 15. In a case where the x and y axes are set on the display surface of the display 15 and the z axis is set in a direction perpendicular to the display surface, the simulation information S0 can be rotated in an arbitrary direction of the three axes. The rotation in the present embodiment means rotation around the z axis. In addition, in a case where rotation other than the rotation around the z axis has been made for the simulation information S0, that is, in a case where rotation around the x axis and/or the y axis has been made for the simulation information S0, the direction of the simulation information S0 is changed. In the present embodiment, the rotation around the x axis and/or the y axis of the simulation information S0 is defined as a direction change.

Here, in a case where the direction of the simulation information S0 is changed, the projection plane of the simulation information S0 is changed. For this reason, the simulation information acquisition unit 22 generates the simulation information S0 again in a case where the direction of the simulation information S0 is changed and the projection plane is changed.

The doctor performs parallel movement, rotation, and enlargement and reduction of the simulation information S0 so that the position of the simulation information S0 matches the position of the liver included in the initial intraoperative image Tf while watching the initial intraoperative image Tf and the simulation information S0 displayed on the display 15. If necessary, the direction of the simulation information S0 is changed. At this time, the transparency of the simulation information S0 may be changed. The transparency of the simulation information S0 may be changed in response to an instruction from the input unit 16, or the transparency of the simulation information S0 may be changed when the doctor performs a touch operation on the display 15 for the initial registration of the simulation information S0.

Then, the doctor gives an instruction to end the initial registration at a time when the position, rotation position, size, and direction of the simulation information S0 match the position of the liver included in the initial intraoperative image Tf, thereby ending the processing of initial registration. An instruction to end the initial registration may be given by operating the input unit 16, or by displaying a button for an end instruction on the display 15, or by performing a predetermined operation, such as a double tap. Then, the initial intraoperative image Tf displayed on the display 15 at the end of the initial registration is stored in the storage device 13.

In the present embodiment, since a surgery target part is the liver, the liver may be excised and moved during the surgery. In the present embodiment, therefore, at the time of initial registration, designation of an invariant position that does not move during the surgery is received in the initial intraoperative image Tf displayed on the display 15. For example, in the initial intraoperative image Tf shown in FIG. 6, a part where a surgical instrument, such as forceps 30, is present does not move during the surgery. In the case of excising the left lobe of the liver, the right lobe of the liver does not move during the surgery. In the present embodiment, therefore, designation of an invariant position that does not move during the surgery, such as a position O1 on the edge of the forceps 30 or a position O2 of the right lobe of the liver, is received through the input unit 16, and the invariant position is stored in the storage device 13.

Then, the first registration unit 24 determines whether or not there has been an instruction to end the initial registration (step ST6). In addition, the second registration unit 25 may perform the processing of step ST6. If the result in step ST6 is negative, the process returns to step ST5 to continue receiving the designation of initial registration. If the result in step ST6 is positive, the second registration unit 25 performs second registration (step ST7).

Figure 7:
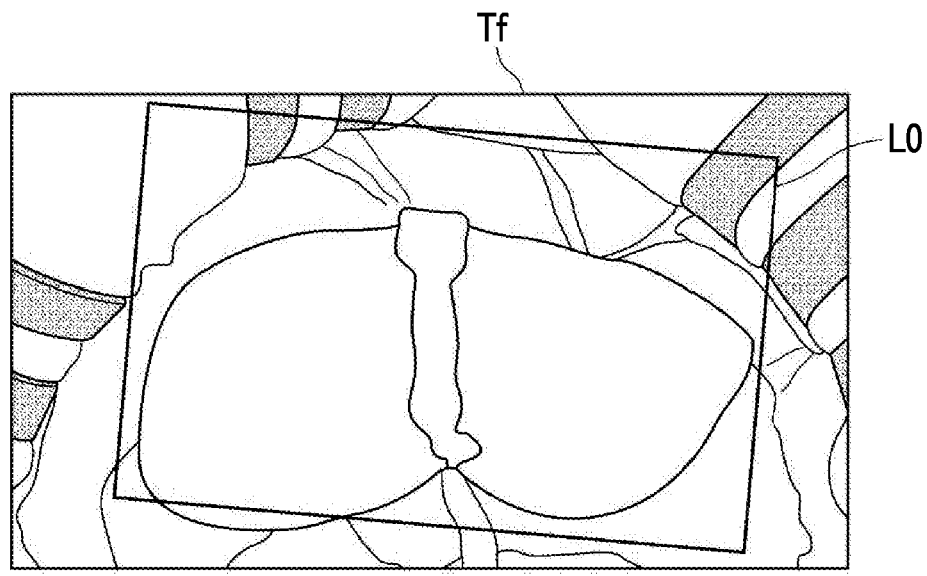
FIG. 7 is a diagram illustrating the shift of the position of an intraoperative image, which is being currently displayed, with respect to an initial intraoperative image.

After the initial registration, the doctor advances the surgery. During the surgery, the doctor cannot always keep the tablet terminal above the subject 7. For this reason, the imaging of the target part using the tablet terminal is temporarily interrupted. Then, when necessary, for example, in order to check the position of a lesion, the liver that is a target part is imaged using the tablet terminal is performed. At this time, the tablet terminal is moved from the position where the initial registration has been performed, and the imaging of the liver is performed again. In such a situation, the position of the camera 14 is shifted from that when acquiring the initial intraoperative image Tf. Therefore, as shown in FIG. 7, the position of the intraoperative video L0 displayed on the display 15 with respect to the initial intraoperative image Tf is shifted. Also in the case of keeping the tablet terminal above the subject 7, the tablet terminal moves as long as the tablet terminal is held by hand. Accordingly, the position of the intraoperative video L0 displayed on the display 15 with respect to the initial intraoperative image Tf is shifted.

The second registration unit 25 acquires position information showing a relative position difference between the initial intraoperative image Tf and an intraoperative image (referred to as T1) forming the intraoperative video L0, which is acquired after the end of initial registration, based on the invariant position described above. In addition, the intraoperative image T1 may be acquired immediately after the end of initial registration, or may be acquired with a delay from the end of initial registration to the extent that there is no problem in observation in a state in which the simulation information S0 and the liver included in the intraoperative video L0 are displayed so as to be superimposed on each other.

In the present embodiment, at the end of the initial registration, the tablet terminal is likely to have moved significantly from the start of the initial registration. For this reason, the second registration unit 25 performs registration between the initial intraoperative image Tf and the intraoperative image T1 using the position information. The registration between the initial intraoperative image Tf and the intraoperative image T1 corresponds to third registration.

Figure 6:
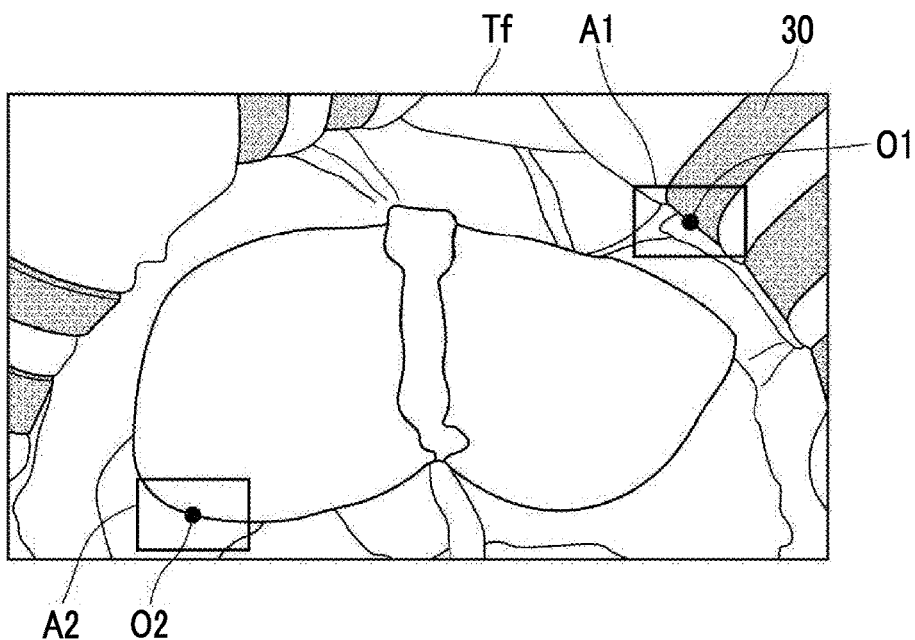
FIG. 6 is a diagram illustrating the setting of a region around an invariant position.

Here, in order to acquire the position information, the second registration unit 25 performs template matching between the intraoperative image T1 and the initial intraoperative image Tf based on an the invariant position. As a method of template matching, it is possible to use a method of setting regions A1 and A2 having invariant positions O1 and O2 at the center, respectively, in the initial intraoperative image Tf as shown in FIG. 6 and calculating at least one of the parallel movement component, the rotational component, or the magnification of the intraoperative image T1 with respect to the initial intraoperative image Tf as position information based on the correspondence relationship between the regions A1 and A2 and the intraoperative image T1. In addition, the rotation means rotation around the z axis, that is, two-dimensional rotation on the xy plane.

Here, the position information indicates a relative position difference between the intraoperative image T1 and the initial intraoperative image Tf. Accordingly, the position information corresponds to the relative position difference between the current position of the camera 14 and the position of the camera 14 at the time of initial registration. The acquisition of position information is not limited to the method of template matching, and may be acquired by calculating the optical flow of the invariant position.

Figure 8:
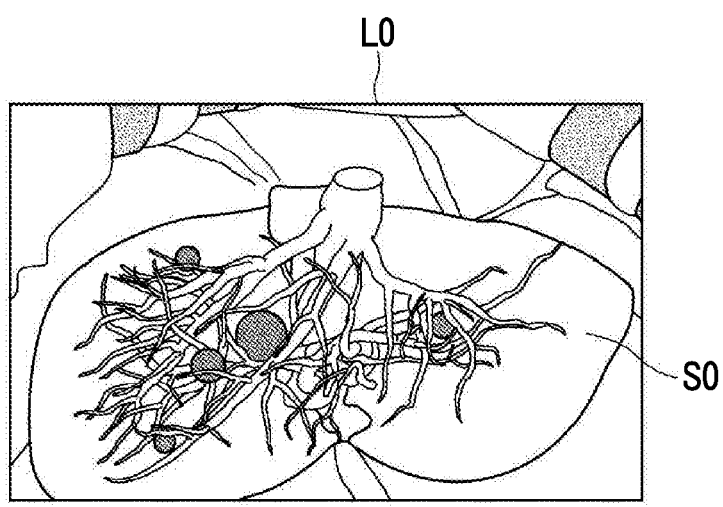
FIG. 8 is a diagram illustrating the superimposed display of simulation information and an intraoperative image.

The second registration unit 25 aligns the initial intraoperative image Tf and the intraoperative image T1 using the position information, and performs second registration using the result of the registration. That is, the simulation information S0 are superimposed on the aligned intraoperative image T1 (step ST8). At this time, parallel movement, rotation, and/or enlargement and reduction of the simulation information S0 are performed based on the position information. As a result, as shown in FIG. 8, the simulation information S0 is superimposed on the intraoperative image T1 at the same position as the position of registration with the initial intraoperative image Tf.

Then, the second registration unit 25 acquires the next intraoperative image that forms the intraoperative video L0 (step ST9). In the present embodiment, the next intraoperative image that forms the intraoperative video L0 is an intraoperative image subsequent to the intraoperative image T1. Then, the second registration unit 25 determines whether or not it is possible to perform second registration by comparing the next intraoperative image (referred to as Tk+1) with the initial intraoperative image Tf (step ST10).

As the surgery progresses, the liver that is a surgery target part is excised, or a part of the liver is moved. As a result, the appearance of the liver included in the initial intraoperative image Tf used at the time of initial registration becomes different from the liver included in the intraoperative video L0 acquired at the present time. For this reason, as the surgery progresses, the second registration may be difficult.

In the present embodiment, therefore, in step ST10, it is determined whether or not it is possible to perform the registration between the simulation information S0 and the liver included in the intraoperative video L0 with the desired accuracy. Specifically, it is determined whether or not an invariant position set in the initial intraoperative image Tf is found in the next intraoperative image Tk+1. If an invariant position is found in the next intraoperative image Tk+1, it is determined that the registration between the simulation information S0 and the liver included in the intraoperative video L0 can be performed with the desired accuracy, and the result in step ST10 is positive.

If the result in step ST10 is positive, the process returns to step ST7 to continue the second registration. At this time, in the second registration processing, the simulation information S0 is aligned with respect to intraoperative images acquired sequentially subsequent to the intraoperative image T1. The second registration is performed using the position information as in the third registration. In this case, it is preferable to calculate the position information from the initial intraoperative image Tf and the intraoperative images acquired in a sequential manner. In addition, between the intraoperative images acquired in a sequential manner, the correspondence relationship between positions corresponding to the invariant positions may be calculated as the position information.

If the result in step ST10 is negative, the second registration unit 25 gives a warning (step ST11) to end the process. As a warning, for example, a text, such as "please redo the initial registration", may be displayed on the display 15, or this text may be output by voice. In addition, warning is not limited thereto, and any kind of warning, such as blinking the screen of the display 15 or generating a beep sound, can be given as long as it can notify a doctor that it is not possible to perform the second registration. By the warning, the operator can redo the initial registration. An instruction to redo the initial registration may be given through the input unit 16. After redoing the initial registration, the processing from step ST3 is performed again.

Thus, in the first embodiment, the initial intraoperative image Tf that is a still image is displayed on the display 15 at the time of initial registration. Accordingly, it is possible to easily perform the registration between the initial intraoperative image Tf and the simulation information S0. In addition, at the time of initial registration, the initial intraoperative image Tf that is a still image is aligned with the simulation information S0, it is possible to quickly perform the first registration processing.

In addition, by performing the initial registration in response to an initial registration instruction input through the input unit 16, it is possible to easily perform the registration between a target part included in the initial intraoperative image Tf and the simulation information.

In addition, by performing the second registration using the result of the third registration, the intraoperative video L0 and the simulation information S0 can be displayed in a state in which the liver included in the intraoperative video L0 and the simulation information S0 are aligned with each other immediately after the end of the initial registration. Therefore, it is possible to perform the subsequent second registration quickly and accurately.

Next, a second embodiment of the invention will be described. In the second embodiment, only the processing performed by the second registration unit 25 is different from that in the first embodiment, and the configuration of the device is the same as that in the first embodiment. Accordingly, detailed explanation of the device will be omitted herein. The second embodiment is different from the first embodiment in that registration between intraoperative images acquired in a sequential manner, which form the intraoperative video L0, is performed until the initial registration ends from the start of the initial registration and that the second registration is performed using the registration result after the end of the initial registration. The registration between the intraoperative images acquired in a sequential manner corresponds to fourth registration.

Figure 9:
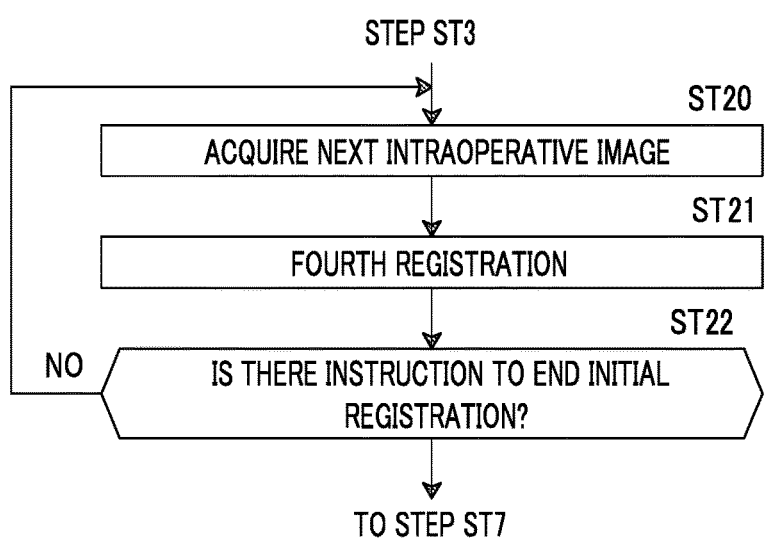
FIG. 9 is a flowchart showing the process performed in a second embodiment.

FIG. 9 is a flowchart showing the process performed in the second embodiment. FIG. 9 shows a flowchart of the process performed in the background of the processing of the initial registration until the initial registration ends from the initial registration instruction in the first embodiment.

Continued to step ST3 of the flowchart shown in FIG. 4, the second registration unit 25 acquires an intraoperative image (referred to as Tk) subsequent to the initial intraoperative image Tf in the intraoperative video L0 (step ST20), and performs fourth registration that is the registration between the initial intraoperative image Tf and the next intraoperative image Tk (step ST21). The fourth registration is performed using the position information, similar to the third registration described above.

Then, as in step ST6 of FIG. 4, the second registration unit 25 determines whether or not there has been an instruction to end the initial registration (step ST22). If the result in step ST22 is negative, the process returns to step ST20 to continue the fourth registration. At this time, an intraoperative image Tk+1 subsequent to the intraoperative image Tk is acquired, and registration between the intraoperative image Tk and intraoperative image Tk+1 is performed. If the result in step ST22 is positive, the process proceeds to step ST7 in the flowchart shown in FIG. 4. The second registration unit 25 performs the second registration using the fourth registration result, so that the simulation information S0 is superimposed on the intraoperative image that has been used in the fourth registration immediately before the instruction to end the initial registration. Position information to be used in this case is calculated by accumulating all pieces of position information acquired by the fourth registration until the initial registration ends from the start of the initial registration. Thus, the intraoperative video L0 and the simulation information S0 can be displayed in a state in which the liver included in the intraoperative video L0 and the simulation information S0 are aligned with each other immediately after the end of the initial registration. Therefore, it is possible to perform the subsequent second registration quickly and accurately.

In the first and second embodiments described above, the movement of the camera 14 may be detected by the motion sensor 17 until the initial registration ends from the start of the initial registration, and the third and fourth registration may be performed using the movement detected by the motion sensor 17 after the end of the initial registration. In the case of performing the third registration, the movement detected by the motion sensor 17 indicates the amount of parallel movement, the amount of rotational movement, and the amount of enlargement or reduction between the initial intraoperative image Tf and an intraoperative image acquired after the end of the initial registration. In the case of performing the fourth registration, the movement detected by the motion sensor 17 indicates the amount of parallel movement, the amount of rotational movement, and the amount of enlargement or reduction between intraoperative images. Accordingly, it is possible to perform the third and fourth registration based on the movement detected by the motion sensor 17. By performing the third and fourth registration using the movement detected by the motion sensor 17 as described above, calculation between images for registration becomes unnecessary. Accordingly, it is possible to reduce the load of processing in the tablet terminal.

In addition, in the first and second embodiments described above, the movement of the tablet terminal, that is, the movement of the camera 14 may be detected by the motion sensor 17, and the second registration may be performed using the detected movement. In this case, the movement of the tablet terminal, that is, the movement of the camera 14 detected by the motion sensor 17 may be a movement between the start time of the initial registration and the present time at which the second registration is performed, or may be a movement between an intraoperative image acquired at the present time and an intraoperative image acquired therebefore. In the former case, the movement detected by the motion sensor 17 indicates the amount of parallel movement, the amount of rotational movement, and the amount of enlargement or reduction between the initial intraoperative image Tf and the intraoperative image at the present time. Accordingly, based on the movement detected by the motion sensor 17, parallel movement, rotational movement, and enlargement and reduction of the simulation information S0 from the initial registration time are performed and the result is superimposed on the intraoperative video L0, thereby performing the second registration. In the latter case, based on the movement detected by the motion sensor 17, parallel movement, rotational movement, and enlargement and reduction of the simulation information S0 from the previous second registration time are performed and the result is superimposed on the intraoperative video L0, thereby performing the second registration.

In the first and second embodiments described above, the initial intraoperative image Tf is displayed on the display 15, so that the operator manually performs the initial registration between the initial intraoperative image Tf and the simulation information S0. However, initial registration between the liver included in the initial intraoperative image Tf and the simulation information S0 may be automatically performed. In this case, since the initial intraoperative image Tf that is a still image is used, it is possible to quickly perform the initial registration.

In the first and second embodiments described above, the intraoperative video L0 and the simulation information S0 are displayed on the tablet terminal so as to be superimposed on each other. However, the invention can also be applied to a case of performing registration between the intraoperative video L0 and the simulation information S0 when displaying the intraoperative video L0 on the head mounted display. In addition, the invention can also be applied to a case of capturing the intraoperative video L0 using a camera located above the operating table and performing registration between the intraoperative video L0 and the simulation information S0 when displaying the image acquired by the capturing on a display in the operating room or a display outside the operating room. In this case, the image registration device 1 according to the present embodiment is installed in a computer, registration between the intraoperative video L0 and the simulation information S0 is performed by the computer, and the intraoperative video L0 and the simulation information S0 are displayed on the head mounted display and the display, which are connected to the computer, so as to be superimposed on each other.

In the first and second embodiments described above, a projected image of the liver extracted from the three-dimensional image V0 is used as the simulation information S0. However, the simulation information S0 is not limited thereto, and a functional three-dimensional image obtained by PET examination, nuclear medical examination, or the like may be used as the simulation information. In addition, the simulation information S0 is not limited to image information, and a line indicating the resection position, symbols such as arrows, text information such as a name of a part or tissue near the resection position, and the like may be used. The image information, the symbols, and the text information may be collectively used as simulation information.

In the first and second embodiments described above, the simulation information acquisition unit 22 generates the simulation information S0. However, the simulation information S0 may also be generated by a simulation information acquisition device provided separately from the image registration device 1. In this case, since the simulation information acquisition unit 22 does not need to generate the simulation information S0, it is possible to simplify the configuration of the device.

In the first and second embodiments described above, the initial registration is performed by performing the parallel movement, rotational movement, enlargement and reduction, and direction change of the simulation information S0. However, a plurality of pieces of simulation information in various directions may be prepared, and simulation information in a direction that matches most the direction of the target part included in the intraoperative video L0 at the time of initial registration may be selected to perform the initial registration.

In the first and second embodiments described above, hepatic arteries or the like included in the liver are extracted to be included in the simulation information S0. However, only the liver that is a surgery target part may be extracted, and an image showing the three-dimensional shape of only the liver may be used as the simulation information S0.

In the first and second embodiments described above, the liver is used as a surgery target part. However, surgery target parts are not limited to the liver, and the invention can also be applied when displaying the intraoperative video L0 and the simulation information S0 so as to be superimposed on each other in a case where an arbitrary part is set as a surgery target.

Hereinafter, the effect of the embodiment of the invention will be described.

By performing the third registration between the intraoperative image for registration and each intraoperative image, which forms an intraoperative video acquired after the end of the first registration, after the end of the first registration and performing the second registration using the result of the third registration, the intraoperative video and the simulation information can be displayed in a state in which the target part included in the intraoperative video and the simulation information are aligned with each other immediately after the end of the first registration. Therefore, it is possible to perform the subsequent second registration quickly and accurately.

By performing the fourth registration between the intraoperative video acquired by image acquisition unit and the intraoperative image for registration until the first registration ends from the start of the first registration and performing the second registration using the result of the fourth registration after the end of the first registration, the intraoperative video and the simulation information can be displayed in a state in which the target part included in the intraoperative video and the simulation information are aligned with each other immediately after the end of the first registration. Therefore, it is possible to perform the subsequent second registration quickly and accurately.

By performing the third registration or the fourth registration using the movement detected by motion detection unit until the first registration ends from the start of the first registration, the intraoperative video and the simulation information can be displayed in a state in which the target part included in the intraoperative video and the simulation information are aligned with each other immediately after the end of the first registration. Therefore, it is possible to perform the subsequent second registration quickly and accurately.

In a case where it is determined that it is not possible to perform the second registration, the operator can take measures, such as performing the first registration again, by giving a warning.

What is claimed is:

1. An image registration device, comprising:
   a processor configured to:
   acquire an intraoperative video that includes a target part of surgery and includes a plurality of intraoperative images captured at different imaging times,
   acquire simulation information relevant to the surgery of the target part,
   acquire an intraoperative image for registration used in registration with the simulation information,
   display the intraoperative image for registration and the simulation information on display such that the intraoperative image for registration and the simulation information are superimposed on each other and performing first registration between the simulation information and the target part included in the intraoperative image for registration,
   perform fourth registration, which performs registration between intraoperative images until an end of the first registration,
   perform second registration, using a result of the first registration and the fourth registration, between the simulation information and the target part included in the intraoperative video, and
   display the simulation information and the target part included in the intraoperative video after the second registration on the display such that the simulation information and the target part included in the intraoperative video after the second registration are superimposed on each other.

2. The image registration device according to claim 1, further comprising:
   an input unit that receives an input of an instruction of the first registration,
   wherein the processor performs the first registration in response to the instruction of the first registration that is input through the input unit.

3. The image registration device according to claim 2,
   wherein the processor performs the second registration after receiving an instruction to end the first registration.

4. The image registration device according to claim 2,
   wherein the processor performs third registration between the intraoperative image for registration and an intraoperative image, which forms the intraoperative video acquired after the end of the first registration, after the end of the first registration and performs the second registration using a result of the third registration.

5. The image registration device according to claim 2, further comprising:
   motion detection sensor that detects movement of imaging camera for imaging the target part to generate the intraoperative image.

6. The image registration device according to claim 2,
   wherein the processor performs the second registration using the movement detected by the motion detection sensor.

7. The image registration device according to claim 1,
   wherein the processor performs the second registration after receiving an instruction to end the first registration.

8. The image registration device according to claim 1,
   wherein the processor performs third registration between the intraoperative image for registration and an intraoperative image, which forms the intraoperative video acquired after the end of the first registration, after the end of the first registration and performs the second registration using a result of the third registration.

9. The image registration device according to claim 8, further comprising:
   a motion detection sensor that detects movement of imaging unit for imaging the target part to generate the intraoperative image,
   wherein the processor performs the third registration using the movement detected by the motion detection sensor until the first registration ends.

10. The image registration device according to claim 1, further comprising:
    a motion detection sensor that detects movement of imaging unit for imaging the target part to generate the intraoperative image,
    wherein the processor performs the fourth registration using the movement detected by the motion detection sensor until the first registration ends.

11. The image registration device according to claim 1, further comprising:

a motion detection sensor that detects movement of imaging camera for imaging the target part to generate the intraoperative image.

12. The image registration device according to claim 1, wherein the processor performs the second registration using the movement detected by the motion detection sensor.

13. The image registration device according to claim 1, wherein the processor performs the second registration by registering the simulation information and the target part included in each intraoperative image that forms the intraoperative image.

14. The image registration device according to claim 1, the processor further configured to:
determine whether or not it is possible to perform the second registration; and
give a warning in a case where it is determined that it is not possible to perform the second registration.

15. The image registration device according to claim 1, wherein the simulation information is an image showing a three-dimensional shape of the target part.

16. The image registration device according to claim 15, wherein the processor is able to change a transparency of an image showing the three-dimensional shape.

17. An image registration method, comprising:
acquiring an intraoperative video that includes a target part of surgery and includes a plurality of intraoperative images captured at different imaging times;
acquiring simulation information relevant to the surgery of the target part;
acquiring an intraoperative image for registration used in registration with the simulation information;
displaying the intraoperative image for registration and the simulation information on display such that the intraoperative image for registration and the simulation information are superimposed on each other and performing first registration between the simulation information and the target part included in the intraoperative image for registration;
performing fourth registration, which performs registration between intraoperative images until an end of the first registration; and
performing second registration, using a result of the first registration and the fourth registration, between the simulation information and the target part included in the intraoperative video and displaying the simulation information and the target part included in the intraoperative video after the second registration on the display such that the simulation information and the target part included in the intraoperative video after the second registration are superimposed on each other.

18. A non-transitory computer readable recording medium storing an image registration program causing a computer to execute:
a procedure of acquiring an intraoperative video that includes a target part of surgery and includes a plurality of intraoperative images captured at different imaging times;
a procedure of acquiring simulation information relevant to the surgery of the target part;
a procedure of acquiring an intraoperative image for registration used in registration with the simulation information;
a procedure of displaying the intraoperative image for registration and the simulation information on display such that the intraoperative image for registration and the simulation information are superimposed on each other and performing first registration between the simulation information and the target part included in the intraoperative image for registration;
a procedure of performing fourth registration, which performs registration between intraoperative images until an end of the first registration; and
a procedure of performing second registration, using a result of the first registration and the fourth registration, between the simulation information and the target part included in the intraoperative video and displaying the simulation information and the target part included in the intraoperative video after the second registration on the display such that the simulation information and the target part included in the intraoperative video after the second registration are superimposed on each other.

* * * * *